US006545171B2

(12) United States Patent
Krafczyk et al.

(10) Patent No.: US 6,545,171 B2
(45) Date of Patent: Apr. 8, 2003

(54) PROCESS FOR THE PRODUCTION OF YELLOW BIS(3-[TRIALKOXYSILY]ALKYL) POLYSULFANES

(75) Inventors: Roland Krafczyk, Rheinfelden (DE); Ulrich Deschler, Sailauf (DE); Björn Treffeisen, Gundelfingen (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/188,033

(22) Filed: Jul. 3, 2002

(65) Prior Publication Data

US 2003/0023106 A1 Jan. 30, 2003

(30) Foreign Application Priority Data

Jul. 6, 2001 (DE) .......................................... 101 32 939

(51) Int. Cl.[7] ................ C07F 7/08; C07F 7/18
(52) U.S. Cl. ...................................................... 556/427
(58) Field of Search .......................................... 556/427

(56) References Cited

U.S. PATENT DOCUMENTS 6,140,524 A * 10/2000 Ichinohe et al. ............ 556/427
6,384,256 B1 * 5/2002 Backer et al. .............. 556/427

* cited by examiner

*Primary Examiner*—Paul F. Shaver
(74) *Attorney, Agent, or Firm*—Smith, Gambrell & Russell, LLP

(57) ABSTRACT

Process for the production of yellow bis(3-[trialkoxy-silyl]alkyl)polysulfanes with an iodine color index of $\leq 10$ mg iodine/100 ml, in which an organic acid is added to neutral chloroalkyltrialkoxysilane and then reacted with sodium polysulfide (NPS) or sodium sulfide ($Na_2S$) and sulfur or sodium polysulfide (NPS) and $Na_2S$ in alcohol.

9 Claims, No Drawings

PROCESS FOR THE PRODUCTION OF YELLOW BIS(3-[TRIALKOXYSILY]ALKYL) POLYSULFANES

INTRODUCTION AND BACKGROUND

The present invention relates to a process for the production of yellow bis(3-[trialdoxysilyl]-alkyl)polysulfanes.

The production of bis(3-[triethoxysilyl]propyl)-tetrasulfanes by reacting chloropropyltriethoxysilane with sodium polysulfide (NPS) is known from DE 21 41 159.

The production of bis(3-[triethoxysilyl]propyl)disulfane by reacting chloropropyltriethoxysilane with sodium polysulfide (NPS) and sodium sulfide ($Na_2S$) is known from DE 10034493.3. Alternatively, bis(3-[triethoxysilyl]-propyl) polysulfanes can be produced by reacting chloropropyltri-ethoxysilane with sodium sulfide ($Na_2S$) and sulfur. The chloropropyltriethoxysilane used in the known processes can be produced by ethanolysis of chloropropyl-trichlorosilane. In this connection a fully reacted product with only a very small proportion of chloropropyl-monochlorodiethoxysilane is obtained according to known processes such as described in DE 20 61 189 and DE 32 36 628. This completely reacted chloropropyltriethoxysilane is hereinafter termed "neutral".

If the neutral chloropropyltriethoxysilane is reacted with sodium polysulfide (NPS, $Na_2S_x$ where x=2 to 5 and mixtures thereof) or sodium sulfide ($Na_2S$) and sulfur or sodium polysulfide (NPS, $Na_2S_x$ where x=2 to 5 and mixtures thereof) and $Na_2S$ for the production of bis(3-[triethoxysilyl] propyl)polysulfanes according to the processes specified above, then a dark yellow to red product (iodine color index $\geq$20 mg iodine/100 ml) is obtained. However, a pale yellow product has been introduced on the market that cannot be obtained from neutral chloropropyltriethoxysilane.

The disadvantage of these known processes is that a product having a dark yellow to red color is obtained.

In order to obtain pale yellow bis(3-[triethoxysilyl]-propyl)polysulfanes (iodine color index $\leq$10 mg iodine/100 ml) a so-called residual acid content in the form of chloro-propylmonochlorodiethoxysilane must be present in the chloropropyltriethoxysilane. This can be achieved if the ethanolysis reaction is not carried out to completion. This procedure introduces a not inconsiderable additional complication in operational practice however, especially since the residual acid content has to be kept within a very narrow range, and the reaction therefore has to be discontinued in a very targeted manner at a specific point shortly before complete conversion.

Also, an acidification of the neutral chloropropyltri-ethoxysilane with alcoholic hydrochloric acid before the reaction with the aforementioned sulfurisation agents does not lead to pale yellow bis(3-[triethoxysilyl]propyl)-polysulfanes, but instead to dark yellow to red bis(3-[triethoxysilyl]propyl)polysulfanes.

The production of pale yellow bis(3-[triethoxysilyl]-propyl)polysulfanes by adding a small amount of chloro-propyltrichlorosilane or chloropropylmonochloro-diethoxysilane or chloropropyldichloromonoethoxysilane to chloropropyltriethoxysilane before addition of the sulfurization agents is known from DE 100 24 037.2 and DE 100 45 269.8.

The disadvantage of this process is that chlorosilanes have to be handled, which on account of their properties are aggressive and highly corrosive compounds that release hydrogen chloride vapors in the presence of moisture.

An object of the present invention therefore is to provide an alternative process by means of which a yellow bis(3-[trialkoxysilyl]alkyl)polysulfane can be obtained and in which the additional use of aggressive chlorosilanes can be dispensed with.

SUMMARY OF THE INVENTION

The above and other objects of the invention can be achieved by a process for the production of yellow bis(3-[trialkoxysilyl]alkyl)polysulfanes with an iodine color index of $\leq$10 mg iodine/100 ml, preferably 5–7 mg iodine/100 ml, which is characterised in that an organic acid, for example formic acid, formyl chloride, acetyl chloride, acetic acid or mixtures of these acids are added to neutral chloroalkyltri-alkoxysilane and then reacted with sodium polysulfide (NPS) or sodium sulfide ($Na_2S$) and sulfur or sodium polysulfide (NPS) and $Na_2S$ in alcohol.

The sodium polysulfide (NPS) may be $Na_2S_x$ where x=2 to 5 or mixtures thereof.

DETAILED DESCRIPTION OF INVENTION

In accordance with the present invention, preferably the bis(3-[trialkoxysilyl]alkyl)polysulfanes may be bis(3-[triethoxysilyl]propyl)polysulfane, bis(3-[triethoxysilyl] ethyl)polysulfane, bis(3-[triethoxysilyl]-methyl) polysulfane, bis(3-[trimethoxysilyl]propyl]-polysulfane, bis(3-[trimethoxysilyl]ethyl)polysulfane or bis(3-[trimethoxysilyl]methyl)polysulfane.

As chloroalkyltrialkoxysilane there can be used chloropropyltriethoxysilane, chloroethyltriethoxysilane, chloromethyltriethoxysilane, chloropropyltrimethoxysilane, chloroethyltrimethoxysilane or chloromethyltrimethoxy-silane. Chloropropyltriethoxysilane may particularly preferably be used.

The yellow bis(3-[trialkoxysilyl]alkyl)polysulfanes that may be produced according to the invention may be a polysulfane mixture. The polysulfane chain can on average contain 1.5–10.0 sulfur, preferably 2.0–4.0 sulfur.

The organic acid can be added in amounts of 0.1–10 wt. %, preferably 0.5–5.0 wt. %, particularly preferably 1.0–5.0 wt. %.

Propanol, ethanol or methanol can be used as alcohol. Preferably the alcohol derived from the alkoxy group may be used as alcohol, for example ethanol in the case of ethoxy groups. Lower alkanols; i.e. containing 1 to 5 carbon atoms are suitable.

The reaction mixture can be heated before addition of sodium polysulfide (NPS) or sodium sulfide ($Na_2S$) and sulfur or sodium polysulfide (NPS) and $Na_2S$, preferably at temperatures of 20–90° C.

The organic acid, for example formic acid or acetic acid, can no longer be detected by means of NMR spectroscopy in the product, namely bis(3-[trialkoxysilyl]alkyl) polysulfane, after the working up, from which it may be assumed that no organic acid remains in the product.

Bis(3-[trialkoxysilyl]alkyl)polysulfanes produced by the process according to the invention have an iodine color index of $\leq$10 mg iodine/100 ml.

The process according to the invention has the advantage that the use of aggressive chlorosilanes can be avoided. The small amount of organic acid required for the production of yellow bis(3-[trialkoxysilyl]alkyl)-polysulfanes may be provided simply by adding for example formic acid or acetic acid to neutral chloropropyl-triethoxysilane. The use of organic acids has the advantage that no hydrogen chloride vapors are released in the presence of moisture.

EXAMPLES

Example 1

2.5 g of formic acid are added dropwise at room temperature to a solution of 240.8 g of chloropropyltriethoxysilane (neutral) in 120 ml of ethanol. 87.1 g of sodium polysulfide (NPS, $Na_2S_4$) are then added and the reaction mixture is boiled for 2 hours under reflux at 82° C. while stirring. After cooling the reaction mixture to room temperature the precipitated sodium chloride is filtered off and the ethanol is removed on a rotary evaporator. A subsequent filtration yields 225.2 g of pale yellow bis(3-[triethoxysilyl]propyl)polysulfane with an iodine color index of 5–7 mg iodine/100 ml, whose identity is confirmed by $^1$H-NMR spectroscopy.

Example 2

2.5 g of formic acid are added dropwise at room temperature to 240.8 g of chloropropyltriethoxysilane (neutral) in 120 ml of ethanol. 18.4 g of sulfur and 44.8 g of sodium polysulfide ($Na_2S_4$) are then added and the reaction mixture is boiled for 2 hours under reflux at 81° C. while stirring. After cooling the reaction mixture to room temperature the precipitated sodium chloride is filtered off and the ethanol is removed on a rotary evaporator. A subsequent filtration yields 210.4 g of pale yellow bis(3-[triethoxysilyl]propyl)polysulfane with an iodine color index of 7–10 mg iodine/100 ml, whose identity is confirmed by $^1$H-NMR spectroscopy.

Example 3

2.5 g of formic acid are added dropwise at room temperature to a solution of 240.8 g of chloropropyltriethoxysilane (neutral) in 120 ml of ethanol. The reaction mixture is boiled for 30 minutes under reflux at 82° C. while stirring. After cooling the reaction mixture to 60° C. 29.1 g of disodium tetrasulfide ($Na_2S_4$) and 26.0 g of sodium sulfide ($Na_2S$) are added and the reaction mixture is boiled for 2 hours at 82° C. under reflux while stirring. After cooling the reaction mixture to room temperature the precipitated sodium chloride is filtered off and the ethanol is removed on a rotary evaporator. A subsequent filtration yields 217.5 g of pale yellow bis(3-[triethoxysilyl]propyl)-polysulfane with an iodine color index of 5–7 mg iodine/100 ml, whose identity is confirmed by $^1$H-NMR spectroscopy.

Example 4

2.5 g of formic acid are added dropwise at room temperature to a solution of 240.8 g of chloropropyltriethoxysilane (neutral) in 120 ml of ethanol. 33.9 g of disodium trisulfide ($Na_2S_3$) and 20.4 g of sodium sulfide ($Na_2S$) are then added and the reaction mixture is boiled for 2 hours under reflux at 82° C. while stirring. After cooling the reaction mixture to room temperature the precipitated sodium chloride is filtered off and the ethanol is removed on a rotary evaporator. A subsequent filtration yields 232.4 g of pale yellow bis(3-[triethoxysilyl]propyl)-polysulfane with an iodine color index of 5–7 mg iodine/100 ml, whose identity is confirmed by $^1$H-NMR spectroscopy.

Example 5

3.3 g of acetic acid are added dropwise at room temperature to a solution of 240.8 g of chloropropyltriethoxysilane (neutral) in 120 ml of ethanol. 87.1 g of sodium polysulfide (NPS, $Na_2S_4$) are then added and the reaction mixture is boiled for 2 hours under reflux at 82° C. while stirring. After cooling the reaction mixture to room temperature the precipitated sodium chloride is filtered off and the ethanol is removed on a rotary evaporator. A subsequent filtration yields 225.0 g of pale yellow bis(3-[triethoxysilyl]propyl)polysulfane with an iodine color index of 5–7 mg iodine/100 ml, whose identity is confirmed by $^1$H-NMR spectroscopy.

Example 6

Comparison Example 1

87.1 g of sodium polysulfide are added at room temperature to a solution of 240.8 g of chloropropyltriethoxysilane (neutral) in 120 ml of ethanol and the reaction mixture is boiled for 2 hours at 82° C. under reflux while stirring. After cooling the reaction mixture to room temperature the precipitated sodium chloride is filtered off and the ethanol is removed on a rotary evaporator. A subsequent filtration yields 255.0 g (94.6%) of red bis(3-[triethoxy-silyl]propyl)polysulfane with an iodine color index of >20 mg iodine/100 ml.

Example 7

Comparison Example 2

18.4 g of sulfur and 44.8 g of sodium sulfide ($Na_2S$) are added at room temperature to a solution of 240.8 g of chloropropyltriethoxysilane (neutral) in 120 ml of ethanol. The reaction mixture is boiled for 2 hours at 82° C. under reflux while stirring. After cooling the reaction mixture to room temperature the precipitated sodium chloride is filtered off and the ethanol is removed on a rotary evaporator. A subsequent filtration yields 209.8 g of red bis(3-[triethoxysilyl]propyl)polysulfane with an iodine color index of ≧20 mg iodine/100 ml, whose identity is confirmed by $^1$H-NMR spectroscopy.

Example 8

Comparison Example 3

29.1 g of disodium tetrasulfide ($Na_2S_4$) and 26.0 g of sodium sulfide ($Na_2S$) are added at room temperature to a solution of 204.8 g of chloropropyltriethoxysilane (neutral) in 120 ml of ethanol and the reaction mixture is boiled for 2 hours at 82° C. under reflux while stirring. After cooling the reaction mixture to room temperature the precipitated sodium chloride is filtered off and the ethanol is removed on a rotary evaporator. A subsequent filtration yields 217.3 g of red bis(3-[triethoxysilyl]-propyl)polysulfane with an iodine color index of ≧20 mg iodine/100 ml, whose identity is confirmed by $^1$H-NMR spectroscopy.

Example 9

Comparison Example 4

33.9 g of disodium trisulfide ($Na_2S_3$) and 20.4 g of sodium sulfide ($Na_2S$) are added at room temperature to a solution of 240.8 g of chloropropyltriethoxysilane (neutral) in 120 ml of ethanol and the reaction mixture is boiled for 2 hours at 82° C. under reflux while stirring. After cooling the reaction mixture to room temperature the precipitated sodium chloride is filtered off and the ethanol is removed on a rotary evaporator. A subsequent filtration yields 232.0 g of red bis(3-[triethoxysilyl]propyl)polysulfane with an iodine color index of ≧20 mg iodine/100 ml, whose identity is confirmed by $^1$H-NMR spectroscopy.

The iodine color index is determined according to DIN 6162.

Further variations and modifications of the foregoing will be apparent to those skilled in the art and are encompassed by the claims appended hereto.

German priority application 101 32 9393 is relied on and incorporated herein by reference.

We claim:

1. A process for the production of a yellow bis(3-[trialkoxy-silyl]alkyl)polysulfane with an iodine color index of $\leq 10$ mg iodine/100 ml, comprising adding an organic acid to neutral chloroalkyltrialkoxysilane and reacting the resulting solution with sodium polysulfide (NPS) or sodium sulfide ($Na_2S$) and sulfur or sodium polysulfide (NPS) and $Na_2S$ in an alcohol in a reaction mixture.

2. The process according to claim 1, wherein the organic acid is added in an amount of 0.1–10 wt. %.

3. The process according to claim 1, further comprising heating the reaction mixture to temperatures of 20–90° C. before addition of sodium polysulfide (NPS) or sodium sulfide ($Na_2S$) and sulfur or sodium polysulfide (NPS) and $Na_2S$.

4. The process according to claim 1, further comprising boiling said reaction mixture before addition of sodium polysulfide (NPS) or sodium sulfide ($Na_2S$) and sulfur or sodium polysulfide (NPS) and $Na_2S$.

5. The process according to claim 1, wherein the yellow bis(3-[trialkoxylsilyl]alkyl)polysulfane is a polysulfane mixtures.

6. The process according to claim 1, wherein the organic acid is formic acid, acetic acid, formyl chloride, acetyl chloride or mixtures of these acids are used as organic acid.

7. The process according to claim 1, wherein the chloroalkyltrialkoxysilane is
chloropropyltriethoxysilane,
chloroethyltriethoxysilane,
chloromethyltriethoxysilane,
chloropropyltrimethoxysilane,
chloroethyltrimethoxysilane or
chloromethyltrimethoxysilane.

8. The process according to claim 1, wherein the alcohol is a lower alkanol.

9. The process according to claim 1 further comprising adding the organic acid to the neutral chloroalkyltrialkoxysilane in an alcohol, then adding the sodium polysulfide or sodium sulfide and sulfur or sodium polysulfide and $Na_2S$ to form a reaction mixture, heating the reaction mixture to boiling for a sufficient period of time to form said polysulfane, cooling the reaction mixture to room temperature, filtering off precipitated sodium chloride and removing said alcohol.

* * * * *